United States Patent [19]
Perkins et al.

[11] Patent Number: 5,200,772
[45] Date of Patent: Apr. 6, 1993

[54] FILTER APPARATUS FOR RETINOSCOPE

[75] Inventors: David G. Perkins, Syracuse; Richard A. Monroe, Liverpool, both of N.Y.

[73] Assignee: Welch Allyn, Inc., Skaneateles Falls, N.Y.

[21] Appl. No.: 757,899

[22] Filed: Sep. 11, 1991

[51] Int. Cl.$^5$ .............................................. A61B 3/10
[52] U.S. Cl. ................................. 351/213; 351/215; 351/221
[58] Field of Search ............... 351/205, 218, 215, 221, 351/213

[56] References Cited
U.S. PATENT DOCUMENTS
4,998,818  3/1991  Kugler et al. .................... 351/205

Primary Examiner—Rodney B. Bovernick
Assistant Examiner—Hung Xuan Dang
Attorney, Agent, or Firm—Wall and Roehrig

[57] ABSTRACT

A retinoscope is provided with a hinged light filter carrier assembly for slidably positioning first and second polarizing filters in the light transmission and viewing passageways. A single actuating lever is provided to move the light filter members into operative position and to retract them out of alignment with the viewing passageways.

11 Claims, 4 Drawing Sheets

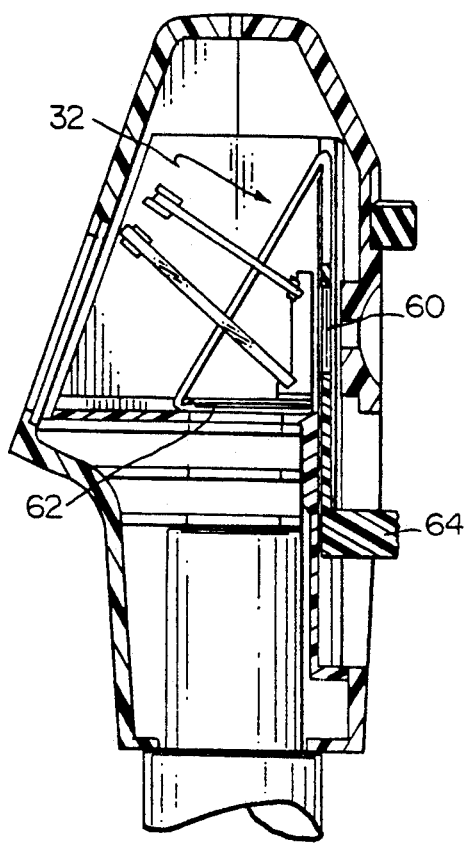
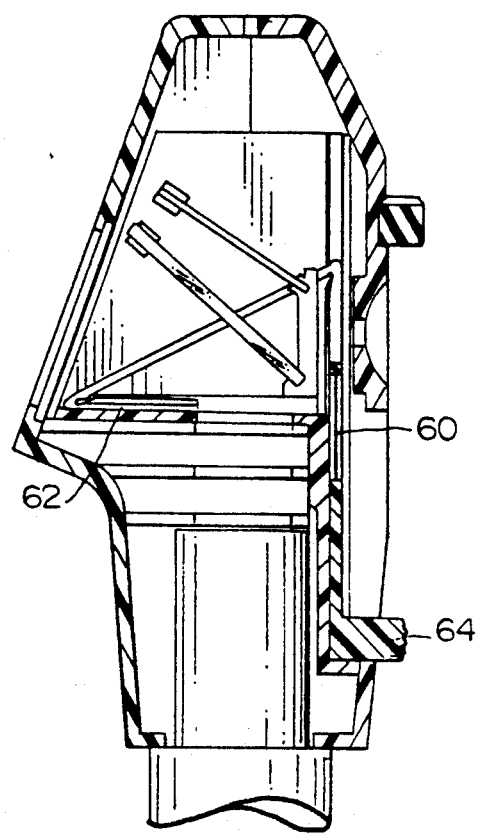
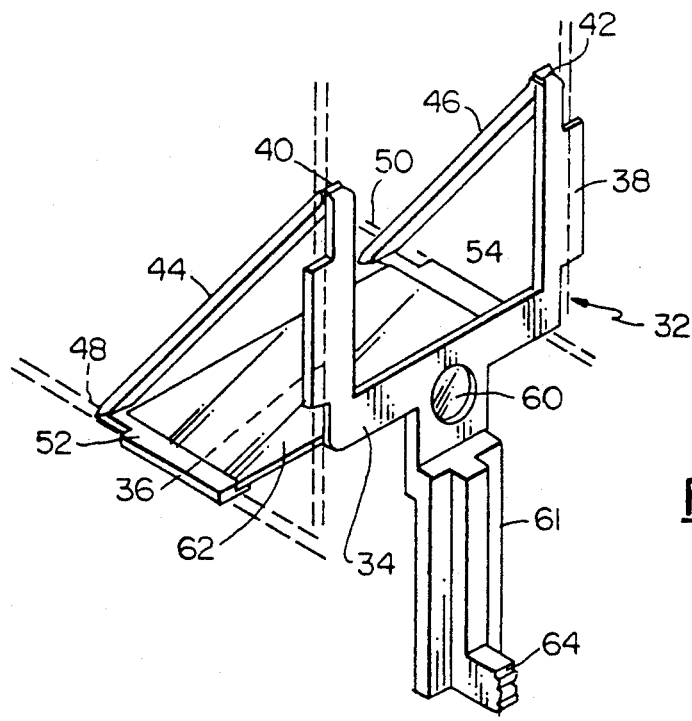
FIG.4  FIG.5
FIG.3

FILTER APPARATUS FOR RETINOSCOPE

BACKGROUND OF THE INVENTION

This invention relates to medical diagnostic instruments and more particularly to a retinoscope having a linear light polarizer filter mechanism for eliminating glare when refracting a patient's eye.

Prior art retinoscopes have heretofore not been equipped with filters for reducing glare. Retinoscopes are used in association with refractors or phoroptors in which a series of trial lenses are placed in the optical path of the instrument to determine a patient's refractive error. These trial lens devices contain a number of different specular lens surfaces as well as sealing windows, all of which can cause glare. Polarized light reflected from specular surfaces such as trial lenses, refractor windows and the cornea of the eye will remain polarized, while light reflected from a diffuse surface, such as the retina of the eye, will lose its polarization. By taking advantage of this phenomena, the glare reflected from specular surfaces in the optical path of a retinoscope can be virtually eliminated by placing a suitable polarization filter in the optical path of the instrument. The term optical path as herein used is broad enough to include both the viewing axis of the instrument and the light path of the instrument which typically are brought together by means of a beam splitter or the like.

Various prior art devices have offered different polarizing filters for the transmitted light and for the viewing light and they have been positioned in place by various levers and knobs. In U.S. Pat. No. 4,998,818 to Kugler et al., which has been assigned to a common assignee together with the present application, there is shown a device for positioning a pair of polarizing filters in the transmission and viewing pathways of an ophthalmoscope by actuation of a single control. This device has proven to be very effective and offers, in addition to the simplified insertion of the polarizing feature, other filter features all actuated by the same control.

The present invention is directed primarily to a retinoscope and provides a simplified single control apparatus for inserting and removing a polarizing filter system into the optical path of the instrument to reduce glare from specular surfaces in the optical path.

OBJECTS AND SUMMARY OF THE INVENTION

Accordingly, it is an object of the present invention to provide a retinoscope with a polarizer assembly that can be simply and easily positioned in and out of the optical path of the retinoscope.

It is another object of the present invention to provide a polarizing assembly for a retinoscope that can be simply and easily and economically manufactured.

It is another object of the present invention to provide a single function control polarizer assembly for a retinoscope having a minimum of individual parts and thus provide for ease of operation and long life.

It is a still further object of the present invention to provide a polarizer assembly for a retinoscope that can be made from simple molded plastic parts while still providing high quality glare-free examination of the retina of the eye.

These and other objects of the present invention are achieved in one embodiment of the invention by the provision of a pair of filters slidably mounted in tracks so that one will be positioned in the light transmission path of an illumination source, and one in the light viewing path of the instrument. The filter members are joined together by a hinged member such that movement of the one filter into operating position will cause the other filter to also move into its operating position.

BRIEF DESCRIPTION OF THE DRAWINGS

For a better understanding of these and other objects of the present invention, reference is made to the detailed description of the invention which is to be read in conjunction with the following drawings, wherein:

FIG. 3 is a perspective view of the filter carrier of the present invention;

FIGS. 4 and 5 are reduced scale cross-sectional views showing the operating and storage positions, respectively of the filter carrier of FIG. 3.

DETAILED DESCRIPTION OF A PREFERRED EMBODIMENT

Figure 1:
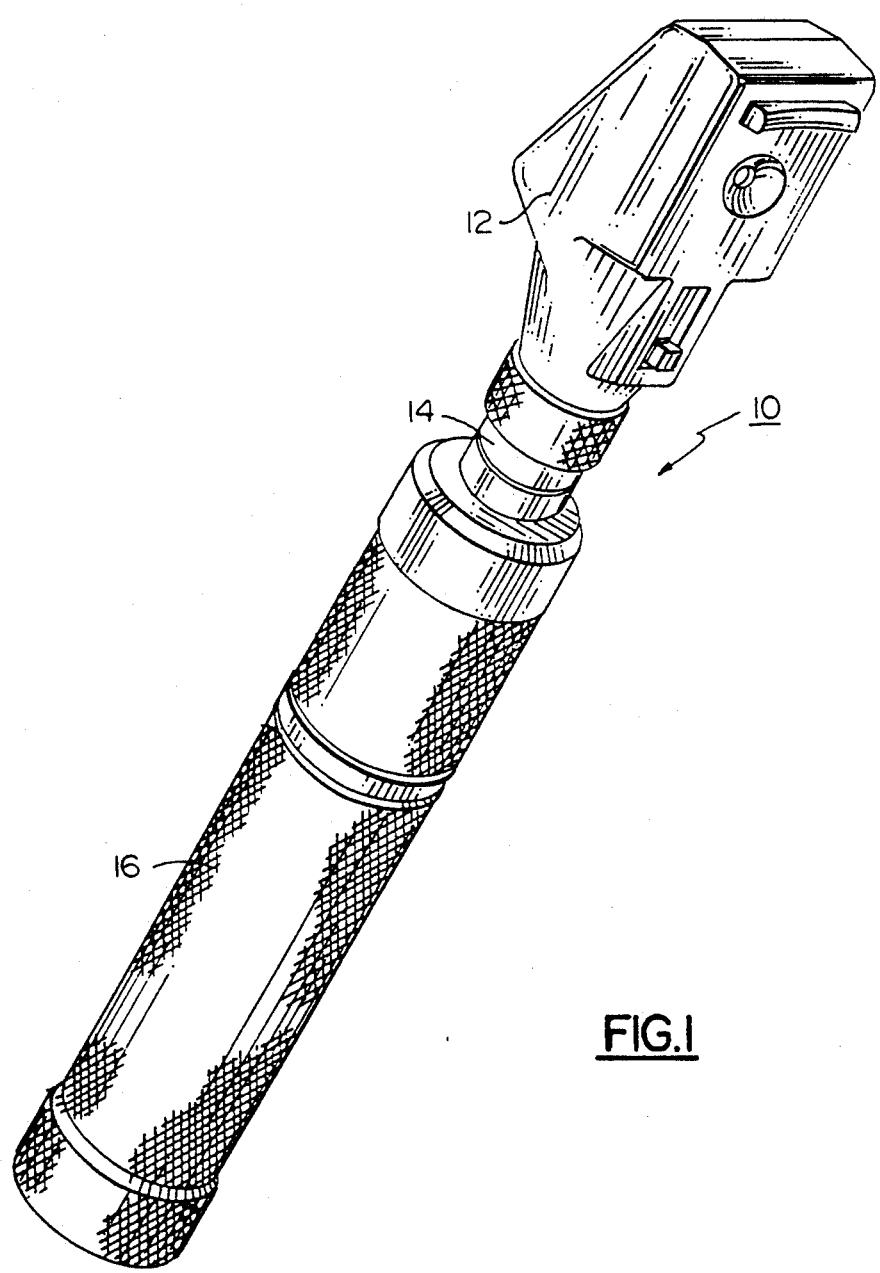
FIG. 1 is a perspective view of a retinoscope in accordance with the present invention.
Figure 2:
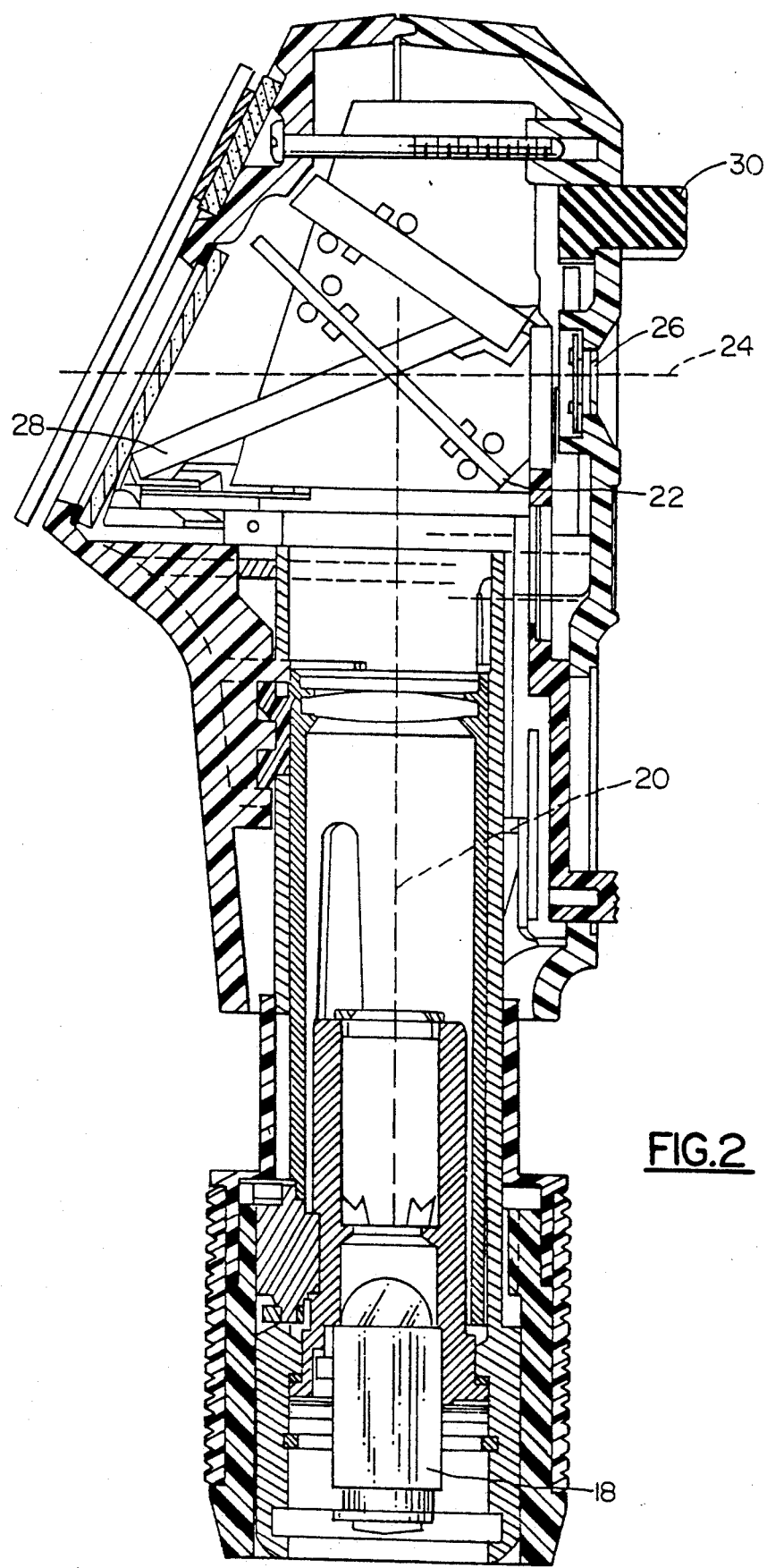
FIG. 2 is an enlarged cross-sectional view of the optical head of the retinoscope of FIG. 1.

Referring now to FIGS. 1 and 2, the retinoscope 10 according to the present invention has a main body portion 12 containing most of the elements of the optical system and a neck 14 that is adapted to be releasably connected to a conventional battery handle 16. As may be seen in FIG. 2, the source of illumination 18 is positioned in the neck 14 and oriented to project a beam of light upward along the dotted line 20 to the mirror or beam splitter 22 for reflection out through the front of the instrument into the patient's eye. A viewing passage 24, again shown by dotted lines, extends from the front face of the instrument through the beam splitter to the physician's eye piece 26 at the back of the instrument. A polarizer/filter carrier assembly 28, shown in FIG. 2 in the inoperative position, will be explained in detail herein. The usual resilient browrest 30 for positioning the instrument on the physician's brow is also provided.

Figure 6:
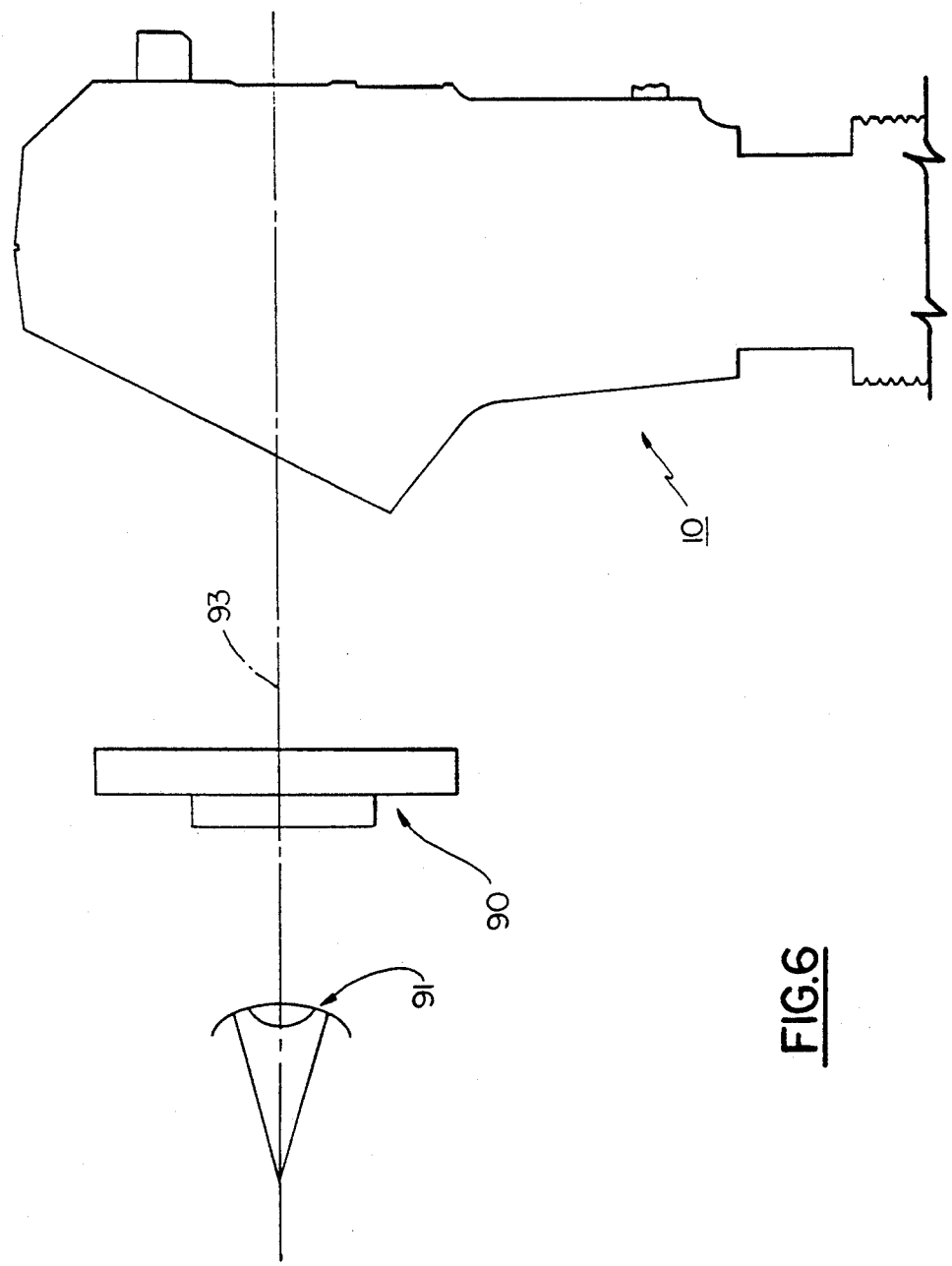
FIG. 6 is a diagrammatic view showing a retinoscope used in conjunction with a refractor.

Turning to FIG. 6, the retinoscope 10 embodying the present invention is shown being used in association with a refractor 90 to view the eye 91 of a patient. As is well known, the refractor is arranged to accept a plurality of different lenses to determine the patient's refractive error. In addition, the refractor typically contains windows, front and rear, situated along the optical axis 93 for protecting the lenses. As noted above, a number of specular surfaces are thus found along the optical axis which can produce unwanted glare.

Referring now to FIG. 3, the polarizer/filter carrier assembly 28 is shown in detail and comprises a frame member 32 having a base portion 34 and two leg portions 36 and 38 which extend upwardly from the base 34 and which have hinge members 40 and 42 connecting the vertical leg members 36 and 38 to slanted linkage members 44 and 46, which extend downwardly at approximately a forty-five degree angle and are further connected by hinges 48 and 50 to horizontal leg members 52 and 54. The entire frame member 32 is made of a plastic material and the hinge members 40, 42, 48 and 50 are of the so-called "living hinge" type which allow the flexing of the frame members at the respective hinge points as the filter carrier is manipulated within the housing, as will be described in more detail herein, in connection with FIGS. 4 and 5.

Mounted in the base portion 34 of the frame member 32 is a polarizing filter element 60 which is adapted to be positioned in and out of the viewing passage of the light reflected from the retina of the patient's eye. A second light polarizing filter element 62 is adapted to be moved in and out of the light transmission path from the light source 18. Obviously, these elements 60 and 62 may be of any desired filter material. In the preferred embodiment, they are linear polarizing filters in which the polarization axis of the element 60 is oriented at ninety degrees to the axis of the element 62 so that polarized light reflected from the trial lens, windows, and the cornea of the patient's eye will be canceled out by the element 60, but light reflected from the retina of the patient's eye will pass through the element 60 since the polarization of the diffused light from element 62 is lost, as it is reflected from the retina.

Referring now to FIG. 4, the frame member 32 is shown with the light polarizing elements in the operative position, i.e., the element 62 being positioned in the light transmission path and the element 60 being positioned in the viewing path. The frame member 32 has a cross-section generally of a right-triangle with the short horizontal leg being the element 62 and the long vertical leg being the vertical uprights 36 and 38 and the element 60. It can be seen that the actuating knob 64 is in the upper position in FIG. 4 indicating that the frame member 32 is in the operative position locating the polarizer elements in the transmission and viewing paths.

FIG. 5 shows the same structure with the actuating knob 64 in the lower position. The frame member 32 forms a right triangle cross-section, but the horizontal leg is now the long leg and the vertical leg is the short leg with the element 62 being retracted to the left in FIG. 5 to a position outside of the light transmission path 20 from the light source 18 and with the element 60 being retracted below the viewing path 24 for the physician's viewing of the light reflected from the patient's retina.

Leg members 36, 38 and 52, 54 have laterally extending flanges which are positioned in cooperating grooves within the housing of the retinoscope head 12 so that the respective legs can only move within the respective tracks, i.e., the legs 36 and 38 can only move vertically, in FIGS. 4 and 5 and the legs 52 and 54 can only move horizontally. Thus, as the rod 61 is moved by knob 64 up and down, the base portion 34 and the element 62 are moved vertically from the operative to inoperative position and vice versa. The hyptenuse, linkage members 44 and 46, of the right triangle push and pull the respective legs 52 and 54 into proper position, since the legs can only move linearly within their slots.

There is thus provided a very simple and economical way to manufacture a mechanism for carrying a pair of polarizing light filter elements into and out of proper alignment for viewing of a patient's eye with a retinoscope. It is apparent from the foregoing that this movement can be accomplished with one finger on the knob 64. The two filters will either both be in place, or they both will be removed.

While this invention has been explained with reference to the structure disclosed herein, it is not confined to the details set forth and this application is intended to cover any modifications and changes as may come within the scope of the following claims.

What is claimed is:

1. An improved retinoscope of the type having a housing with a viewing path passing therethrough, a source of illumination for directing a beam of light along a light path and reflecting means redirecting the light path along the viewing path the improvement comprising:

a first filter means slidably mounted within the housing so that said first filter means may be towed into and out of the viewing path, said first filter means being positioned behind the reflecting means so that said first filter means is not in the light path of the source;

a second filter means slidably mounted within the housing so that said second filter means may be moved into and out of the light path between the light source and the reflecting means;

a hinged frame means for slidably and dependently containing said first and second filter means within the housing; and actuating means connected to said hinged frame means for selectively moving said first filter means into and out of the viewing path while dependently moving said second filter means into and out of the light path so as to modify the light observed along the viewing path.

2. The improvement according to claim 1 wherein said hinged frame means includes a pair of spaced linkage members that are hinged at one end to said first filter means and at the other end to said second filter means.

3. The improvement according to claim 2 wherein said filter means are mounted perpendicularly to each other and said linkage members are connected at the remote end of each filter means.

4. The improvement according to claim 3 wherein each filter means includes a pair of laterally disposed flanges, a pair of linear grooves formed in the housing for receiving the flanges associated with each of said filter means, each pair of linkage members being hinged to said filter means whereby sliding movement of one filter means causes a similar movement in the other filter means.

5. The improvement according to claim 4 wherein each of said pair of grooves is disposed at approximately right angles relative to each other with one pair being vertically disposed and the other pair being horizontally disposed.

6. The improvement according to claim 5 wherein each member of said pair of linkage members is hingedly connected at one to the outer edge of said second filter means and at the other end to the upper edge.

7. The improvement according to claim 6 wherein said pair of linkage members form the hypotenuse of a right triangle with said first and second filter means selectively forming the longer or shorter legs of the triangle depending on whether the filter means are positioned in or out of the viewing path.

8. The improvement according to claim 1 wherein said first and second filter means are positioned at right angles so as to block reflection when placed in the viewing path.

9. A retinoscope having a housing, a viewing passage therethrough, and illumination source positioned to project a beam of light through said viewing passage, a multiple light filter carrier assembly comprising
- a first light filter mounted in a first frame section for sliding movement in a first plane,
- a second light filter mounted in a second frame section for sliding movement in a second plane,
- a third frame section hingedly joined to said first frame section at one end and hingedly joined to said second frame section at the other end, and actuating handle means connected to said second frame section at the end opposite the hingedly joined end thereof.

10. An apparatus according to claim 8 wherein said first and second frames are mounted at approximately right angles to each other.

11. An apparatus according to claim 10 wherein said first, second and third frame sections, when hingedly joined together and mounted for relative sliding movement, form in cross section a right triangle with a depending leg.

* * * * *

UNITED STATES PATENT AND TRADEMARK OFFICE
CERTIFICATE OF CORRECTION

PATENT NO. : 5,200,772
DATED : April 6, 1993
INVENTOR(S) : David G. Perkins

It is certified that error appears in the above—identified patent and that said Letters Patent is hereby corrected as shown below:

Col. 4, line 9, please delete "towed" and insert --moved--;

line 54, after "one", please insert --end--;

line 56, after "edge", please insert --of said first filter means--;

Signed and Sealed this

Third Day of May, 1994

Attest:

BRUCE LEHMAN

Attesting Officer          Commissioner of Patents and Trademarks